United States Patent [19]

Ikeda

[11] Patent Number: 5,572,026
[45] Date of Patent: Nov. 5, 1996

[54] METHOD FOR PREPARATION OF TRANSMISSION ELECTRON MICROSCOPE SAMPLE MATERIAL UTILIZING SHEET MESH

[75] Inventor: Yuji Ikeda, Kanagawa, Japan

[73] Assignee: Sony Corporation, Japan

[21] Appl. No.: 422,313

[22] Filed: Apr. 13, 1995

Related U.S. Application Data

[62] Division of Ser. No. 112,718, Aug. 27, 1993, Pat. No. 5,440,123.

[30] Foreign Application Priority Data

Sep. 3, 1992 [JP] Japan ................................ 4-235026

[51] Int. Cl.⁶ .................................................. H01J 37/20
[52] U.S. Cl. ................. 250/307; 250/442.11; 250/491.1
[58] Field of Search ...................................... 250/307, 311, 250/440.11, 442.11, 491.1

[56] References Cited

U.S. PATENT DOCUMENTS

| | | | |
|---|---|---|---|
| 4,596,934 | 6/1986 | Yanaka et al. | 250/442.11 |
| 4,618,767 | 10/1986 | Smith et al. | 250/311 |
| 4,992,661 | 2/1991 | Tamura et al. | 250/309 |
| 5,225,683 | 7/1993 | Suzuki et al. | 250/442.11 |
| 5,280,178 | 1/1994 | Engelen et al. | 250/440.11 |
| 5,306,918 | 4/1994 | Goudonnet et al. | 250/442.11 |
| 5,440,123 | 8/1995 | Ikeda | 250/311 |

*Primary Examiner*—Bruce C. Anderson
*Attorney, Agent, or Firm*—Ronald P. Kananen

[57] ABSTRACT

A method for processing sample material for use with transmission electron microscopes utilizes a sheet mesh for supporting the sample material during irradiation processing. The sheet mesh is formed of a metallic sheet material having a single opening provided in a central portion thereof, a circumferential edge portion of the opening is tapered from one side of the sheet mesh through to the other and the angle of the taper corresponds to the angle of irradiation. Position determining portions are provided on the sheet mesh to assure reliable positioning of the sample material. Also, the method provides a for preparation of the sample material including a protective layer formed over a membrane layer for allowing adhesion of membrane layers made of materials which would otherwise degrade the adhesion layer during processing.

11 Claims, 8 Drawing Sheets

METHOD FOR PREPARATION OF TRANSMISSION ELECTRON MICROSCOPE SAMPLE MATERIAL UTILIZING SHEET MESH

This application is a division of application Ser. No. 08/112,718 filed Aug. 27, 1993 U.S. Pat. No. 5,440,123.

BACKGROUND OF THE INVENTION

1. Field of the Invention

The present invention relates generally to a sheet mesh for holding samples for examination by TEM (Transmission Electron Microscope). Specifically, the present invention relates to a method of processing such sample material utilizing the sheet mesh for supporting the material during processing.

2. Description of the Prior Art

Figure 14:
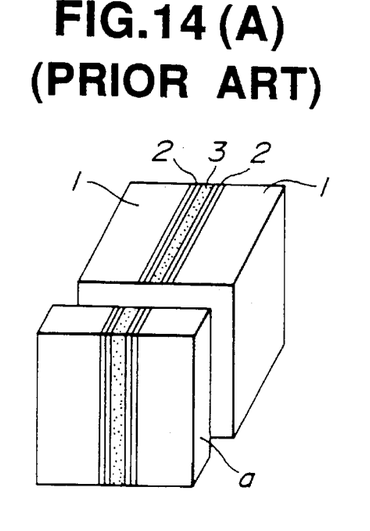
FIGS. 14A–D show sequential views of a conventional processing method for transmission electron microscope sample material including a sheet mesh portion and irradiation apparatus therefor.

For appraising the minute structures of modern semiconductor devices, a cross-section of the elements of such devices must be examined under high magnification, generally by way of a transmission electron microscope (TEM) or the like. Referring to FIGS. 14(A)–(D), a conventional method of processing sample material for such a process will be explained in detail. First, referring to FIG. 14(A), first and second substrates 1, 1 have membranes layers 2, 2 applied to one side thereof respectively. The first and second substrates 1, 1 are arranged such that the membrane layers 2, 2 thereof face each other and are joined therebetween via an adhesion layer to form a block of sample material a. Then, a thin wafer of the sample material a is cut from the main block, such that the membrane layers 2, 2 and the adhesion layer 3 run lengthwise substantially through the center of the sample material a. The sample material a is then attached to a rotatable polishing apparatus 4 via a bonding layer 5. The surface of the sample material a is then exposed to a polishing powder 6 under pressure applied from the opposite side by the rotatable polishing apparatus 4, as seen in FIG. 14(B) such that thickness of not more than 20 μm is achieved and both sides are given a mirror finish.

Then, for processing of the sample material, as seen in FIG. 14(C), the wafer of sample material a is placed over an opening 7a provided in a single hole mesh 7 (sheet mesh) formed of a metallic sheet material and having a thickness of 10 um, for example. Referring to FIG. 14(D), the sheet mesh 7 with the sample material a thereon is mounted on a rotation apparatus 8 and is then rotated under vacuum conditions while being irradiated by a high pressure electrical discharge, as for example an $Ar^+$ ion beam B, at an irradiation angle of 9°–20°. Irradiation is continued until a small hole is formed in the center of the wafer of sample material a, and at this, a finished sample for use with a transmission electron microscope is completed.

Figure 15:
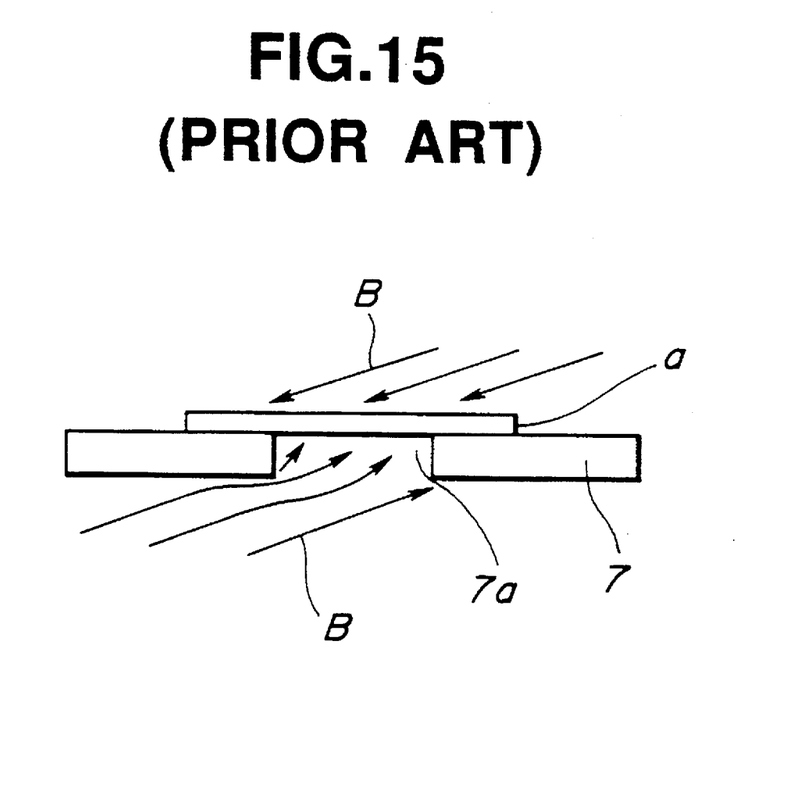
FIG. 15 shows conventional irradiation processing according to the method shown in FIG. 14.
Figure 16:
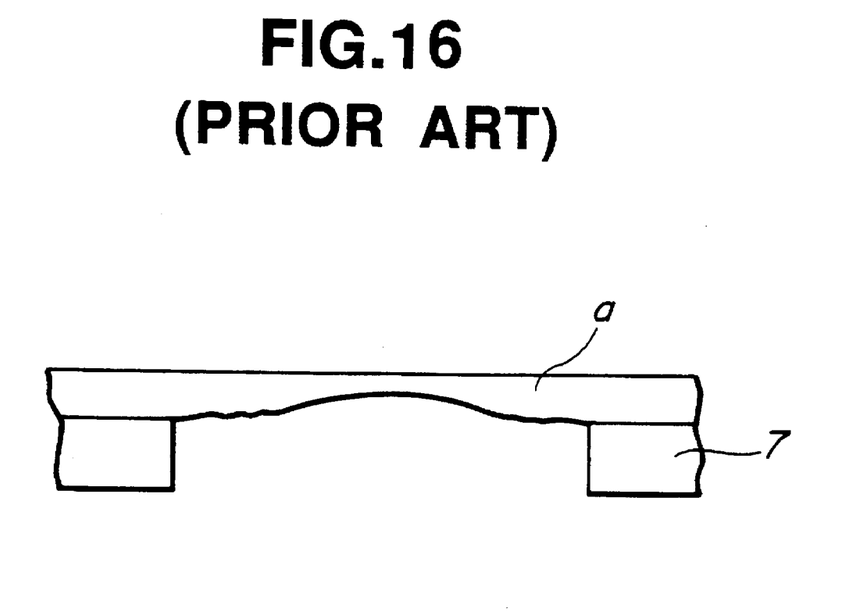
FIG. 16 is a cross-sectional view of sample material after processing according to the conventional method of FIGS. 14 and 15.

According to such conventional processing of sample materials for transmission electron microscopes, as seen in FIG. 15, when irradiation is carried out, the beam B is reflected by corners and edges of the openings 7a of the sheet mesh 7. This causes turbulence in the ion flow irradiating the sample material and, as seen in FIG. 16, a circumference of the small hole formed in the sample material a may receive insufficient irradiation, or unevenness and/or pitting may occur in the finish of the irradiated surface, degrading sample quality.

Further to this, the efficiency of the adhesion layer 3, used to bind the sample material a together, is dependent on the qualities of the membrane layers 2, 2. Thus a problem in which sufficient irradiation may not be obtained due to degradation of the adhesion layer is present. Also, under such conditions, lifting of Al, or another material forming the sample material a may occur.

Figure 17A:
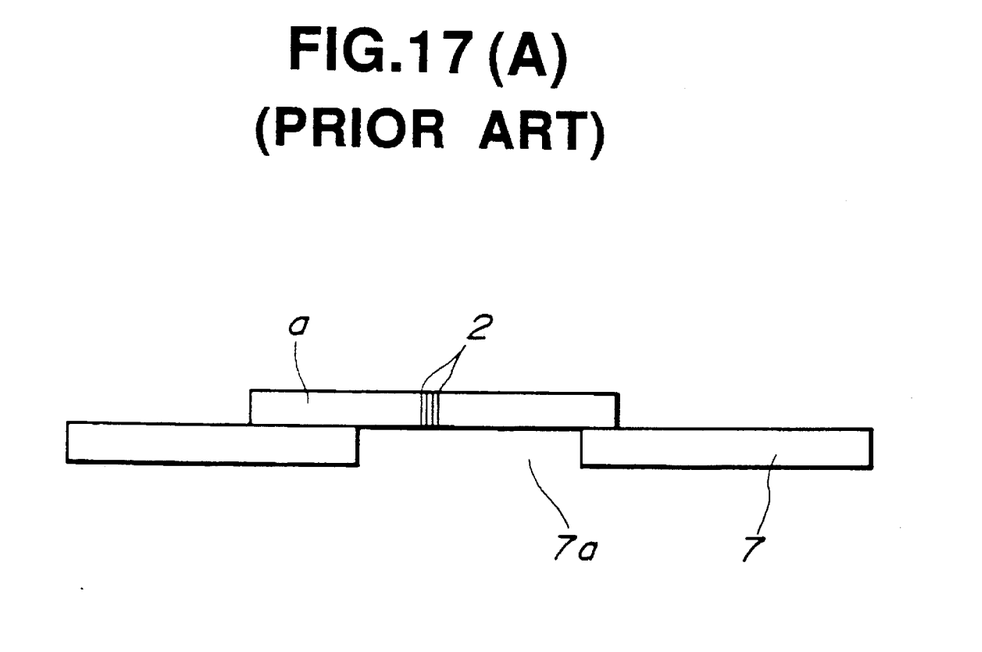
Figure 17B:
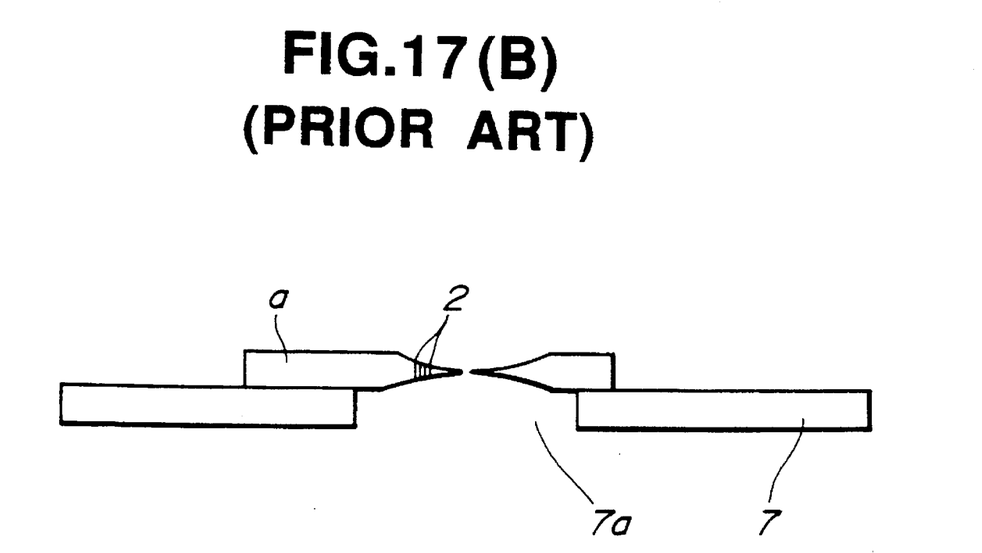

Utilizing the above method, examination of an object to be observed by a transmission electron microscope, the membrane layer 2 for example, which must be positioned over the opening 7a of the sheet mesh 7, becomes difficult. Referring to FIG. 17(A) a condition is shown in which the positioning of the wafer of sample material a has slipped relative the surface of the sheet mesh 7 resulting, as seen in FIG. 17(B) in insufficient irradiation being applied to the portion to be examined, that is the membrane layers 2, 2.

Thus it has been required to provide a method for processing sample material for use with transmission electron microscopes in which optimal irradiation characteristics are provided during preparation of sample material. Also, a processing method is required in which positioning of the sample material is reliably assured and in which the adhesion characteristics between layers of the sample material are efficiently maintained.

SUMMARY OF THE INVENTION

It is therefore a principal object of the present invention to overcome the drawbacks of the prior art.

It is a further object of the present invention to provide a sheet mesh which provides optimal irradiation conditions for a sample material and which may assuredly position the sample material relative an irradiating beam.

It is a further object of the invention to provide a method for processing sample material for a transmission electron microscope in which adhesion between layers of sample material is efficiently maintained such that a high level of processing quality may be reliably assured and peeling of layers of the sample material is prevented.

In order to accomplish the aforementioned and other objects, a method for irradiation processing of laminate material used in a semiconductor device is provided, comprising the steps of: providing first and second substrates, applying a material layer to at least one surface of the first and second substrates, applying a protective layer over the material layers, joining the material layers of the first and second substrates via an adhesion layer to form a laminate, cutting the laminate to a predetermined dimension such that the material and adhesion layers form a line substantially through a center thereof, forming an opening between first and second surfaces of a sheet mesh, tapering edge portions of the opening between the first and second surfaces at a predetermined irradiation angle, mounting the laminate over the opening on the first surface of the sheet mesh, irradiating the laminate via an energy beam at the irradiation angle through the opening in the sheet mesh.

According to another aspect of the present invention, a sheet mesh for irradiation processing is provided, comprising: a sheet mesh for mounting a sample material for irradiation processing via an energy beam, the sheet mesh having an opening formed through a substantially center portion thereof between first and second opposed surfaces, and, a tapered portion formed at edge portions of the opening between the first surface and the second surface.

Further, according to still another aspect of the invention, a sheet mesh for transmission electron microscope sample material comprises: a sheet mesh capable of holding the sample material for the transmission electron microscope at time of polishing via an energy beam, the sheet mesh having an circular opening formed through a substantially center portion thereof, first and second opposed surfaces, the opening extending from the first surface through the sheet mesh to the second surface, the sample material being mountable on the first surface, a contoured portion formed at an edge of the opening circumferentially in an area between the first surface and the second surface such that the second surface does not intersect an angle of irradiation by the energy beam.

Yet another aspect of the present invention embodies a method for processing sample material for use with a transmission electron microscope, comprising the steps of: cutting a portion out of the sample material to be used with the transmission electron microscope, mounting the sample material on a first surface of a sheet mesh, providing an opening in the sheet mesh from the first surface to a second surface opposite the first surface, a gradient of an edge portion of the opening being formed with a predetermined taper from the first surface to the second surface, irradiating the sample material via an energy beam directed through the opening in the sheet mesh.

A still further embodiment of the principle of the invention may be realized in a sheet mesh for processing sample material for use with a transmission electron microscope, comprising: a metallic sheet mesh having an opening provided in a substantially center portion thereof, and positioning determining means provided on a side of the sheet mesh on which the sample material is to be supported.

The invention may further be realized as a method for processing sample material for use with a transmission electron microscope, comprising the steps of: cutting a portion of the sample material, defining an opening in a layer of sheet mesh, forming a positioning indication on one side of the sheet mesh, mounting the portion of the sample material on the side of the sheet mesh so as to be set at a predetermined position indicated by the positioning indication, and irradiating the sample material via an energy beam via the opening.

Another method according to the invention for processing sample material for use with a transmission electron microscope, comprises the steps of: cutting a portion of the sample material, defining an opening in a layer of sheet mesh, forming a recessed portion on one side of the sheet mesh substantially around the opening, inserting the portion of the sample material into the recessed portion, and irradiating the sample material via an energy beam via the opening.

Also according to the invention, a transmission electron microscope sample material is provided, comprising: first and second semiconductor substrates, at least one of the substrates having a membrane layer formed thereon, a protective layer formed over the membrane layer, an adhesive layer joining the first and second substrates, the adhesive layer being adjacent the protective layer.

And, the invention further teaches a method for processing sample material for use with a transmission electron microscope, comprising the steps of: providing first and second substrates, applying an subject layer to at least one surface of the first and second substrates, applying a protective layer over the subject layers, joining the subject layers of the first and second substrates via an adhesion layer to form a sample, cutting the sample to a predetermined dimension such that the subject and adhesion layers form a line substantially through a center thereof, forming an opening between first and second surfaces of a sheet mesh, marking the first surface of the sheet mesh with a positioning indication, mounting the sample over the opening according to the positioning indications, and irradiating the sample via an energy beam through the opening in the sheet mesh.

BRIEF DESCRIPTION OF THE DRAWINGS

In the drawings:

FIG. 18 is a perspective view of the sheet mesh portion of FIG. 12 showing a concave portion thereof;

FIGS. 17 A and B are cross-sectional views of a conventional processing method for transmission electron microscope sample material, illustrating a drawback of the conventional process.

DESCRIPTION OF THE PREFERRED EMBODIMENT

Figure 1:
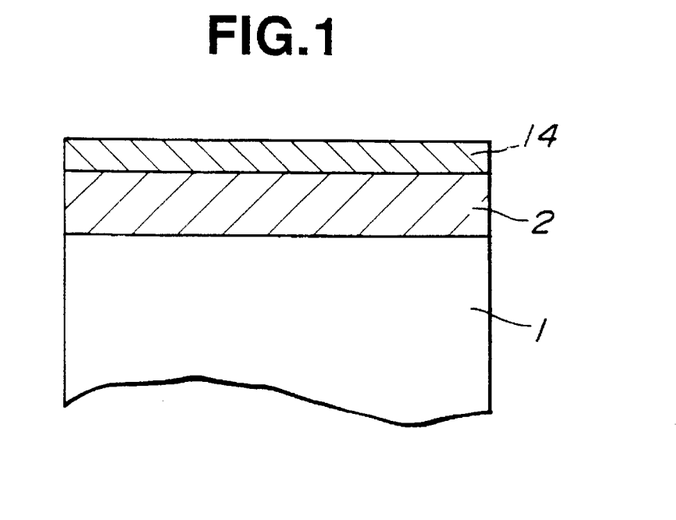
FIG. 1 is a cross-sectional view of a composition of sample material for a transmission electron microscope according to the method of the invention.
Figure 2:
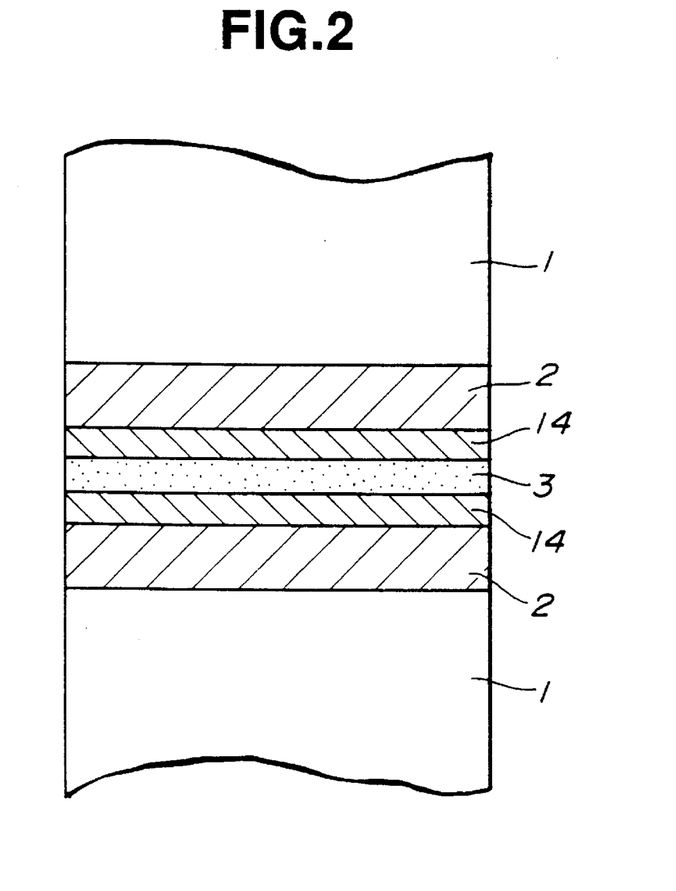
FIG. 2 is a cross-sectional view of a composite of sample material according to the method of the invention, wherein an adhesion layer is formed along an axial center of the layer of sample material.

Referring now to the drawings, particularly to FIGS. 1 and 2, preparation of a sample material A for processing according to the method of the invention will be explained in detail.

As noted above in relation to the conventional process shown in FIGS. 14(A) to (D), an efficiency of a adhesion layer 3 utilized to adhere the membrane layers 2, 2 of the sample material A is dependent on the qualities of the membrane layers 2, 2. Thus sufficient irradiation may of the sample material may not be possible due to degradation of the adhesion layer, or lifting of a material, such as aluminum (Al), or another material forming the membrane layer 2 of the sample material.

Thus, according to the method of the invention, and as seen in FIG. 1, a fine protection layer 14, of SiN, for example, is formed over the membrane layer 2, which is formed on the semiconductive substrate 1. The membrane layer 2 may be applied by ordinary techniques for construction of semiconductor devices, and the protection layer 14 may also be applied according to standard procedures, such as CVD for example. According to the present embodiment, a thickness of the protection layer may be determined at 500 nm, while the thickness of the membrane layer 2 may be determined according to a design of the particular semiconductor device to be examined.

According to the above, and referring now to FIG. 2, two facing sample pieces comprising a semiconductor substrate layer 1, a membrane layer 2 and a protection layer 14 are arranged facing each other and adhered by a adhesion layer 3, of epoxy, for example. According to this, the adhesion layer 3 directly binds together the facing protection layers 14, 14 of the opposing sample pieces. According to this, membrane layers which, according to the conventional method described hereinbefore, it would not be possible to adhere, may be reliably adhered and thus it is possible to use membrane layers 2 of such composition as sample material for examination under a transmission electron microscope.

Further, although the above described composition of the sample material A is described optimal for preventing peeling of a membrane layer 2 of aluminum, the method of preparation of sample material according to the method of the invention is not limited to membrane layers 2 of Al, but of any other material utilized in such application. It will further be noted that, although a protection layer 14 of SiN is taught above, the material of the protection layer is not limited to this material, but may be of any other material selected in view of the composition of the membrane layer 2. Of course, the material of the adhesion layer 3 need not be limited to epoxy, any other suitable adhesive may also be used and, although in the above example, a layer of semiconductor substrate is provided on both sides of the sample material A, it may alternatively be provided on only one side.

Figure 3:
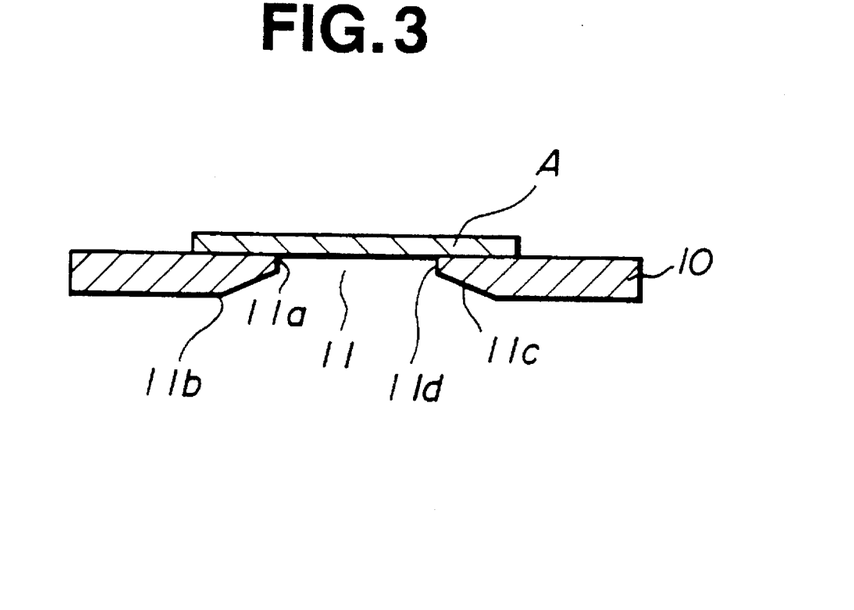
FIG. 3 is a cross-sectional view of a first embodiment of a sheet mesh according to the processing method for transmission electron microscope sample material according to the invention.
Figure 4:
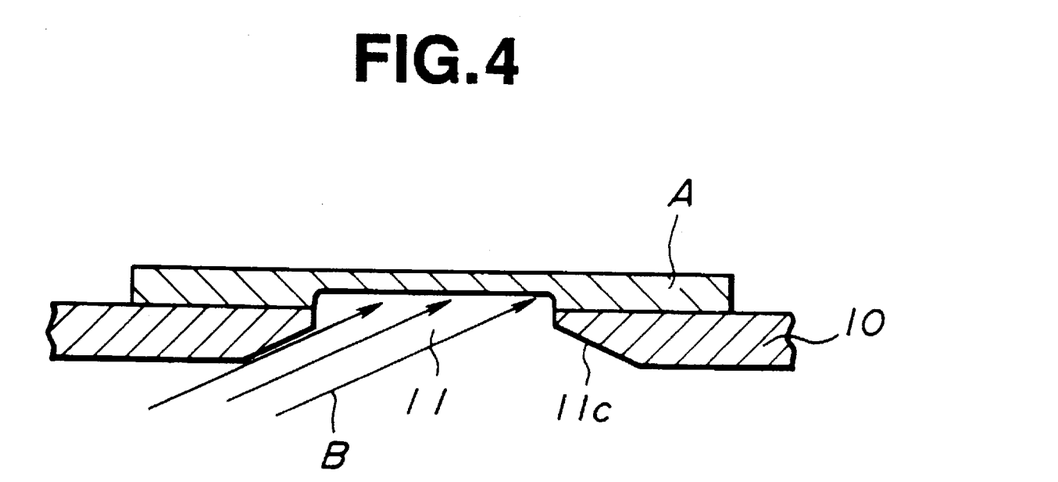
FIG. 4 is a cross-sectional view of the first embodiment showing irradiation processing of the sample material.

Hereinbelow, a structure of a sheet mesh 10 utilized for irradiation processing will be described in detail. FIG. 3 shows a cross-sectional view is shown of a sheet mesh (single hole mesh) 10 having positioned on one surface thereof a wafer of prepared sample material A. At a center portion of the sheet mesh 10, a circular opening 11 is defined between an upper (first) circumferential edge 11a and a lower (second) circumferential edge 11b. For processing, the sample material A is positioned so as to cover the opening 11 of the sheet mesh 10. Further, a tapered portion 11c is formed circumferentially around an area between the upper edge 11a on which the sample material A is supported and the lower edge 11b. According to the present embodiment, a circumferential portion 11d of the upper edge 11a of the opening 11 is not tapered and, as seen in FIG. 4, an angle of the tapered portion 11c is determined to be the same as an angle of an energy beam B, an argon (Ar) ion beam for example, utilized for irradiating the sample material. It will also be noted that such a sheet mesh structure as described above is applicable for processing of conventionally prepared sample material as described hereinbefore referring to FIGS. 14(A) and 14(B).

As in the conventional process shown in FIG. 14(D), the sheet mesh 10 with the sample material A thereon is mounted on a rotation apparatus 8 and is then rotated under vacuum conditions while being irradiated by the energy beam B.

According to the structure of the sheet mesh 10 having the tapered portion 11c formed between edges 11a, 11b at each side of the opening 11, irradiation of the sample material A may be carried out without occurrence of collision of ions from the energy beam B with edges of the opening 11 of the sheet mesh 10. Thus, irradiation characteristics are enhanced and a higher quality sample material A may be obtained. Further, the tapered portion 11c allows smooth uniform flow of the energy beam without turbulence and prevents a portion of the sheet mesh 10 itself from being inadvertently irradiated in the vicinity of where the sample material A is placed. Thus, contamination of the sample material A by the material of the sheet mesh 10 is prevented.

FIGS. 5 to 9 show various alternative embodiments of a sheet mesh utilized in the method of processing sample material for transmission electron microscopes according to the invention.

Figure 5:
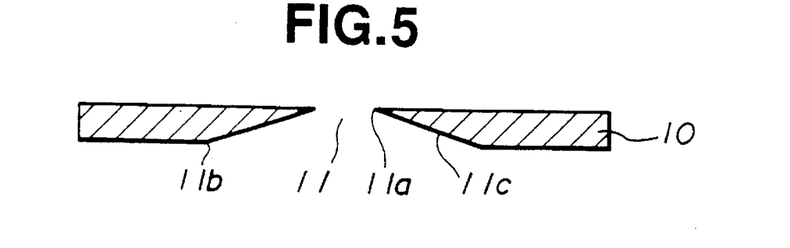
FIG. 5 is a cross-sectional view of a modification of a sheet mesh portion according to the invention.

In FIG. 5, a alternative formation of a sheet mesh 10 is shown. According to this embodiment, an entire area between the upper edge 11a and the lower edge 11b of the opening 11 is taken up by the tapered portion 11c, that is, the untapered circumferential portion 11d is not present. According to this, more complete and defined irradiation of the sample material A is possible without occurrence of 'shadowing' of the energy beam B. As in the previous embodiment, the tapered portion 11c is at an angle corresponding to an irradiation angle of the energy beam B.

Figure 6:
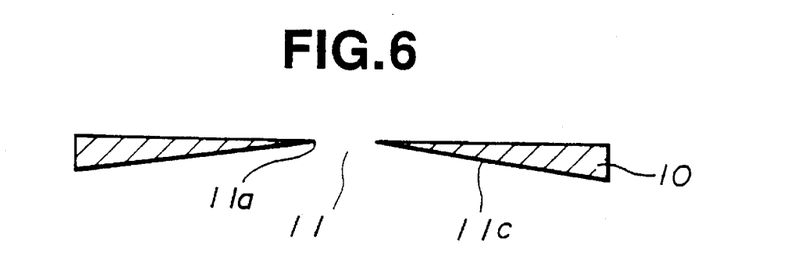
FIG. 6 is a cross-sectional view of an alternative modification of a sheet mesh portion according to the invention.

FIG. 6 shows a formation of the sheet mesh 10 in which the tapered portion 11c takes up the entire lower area of the sheet mesh 10. The taper angle may be formed lower than the angle of irradiation.

Figure 7:
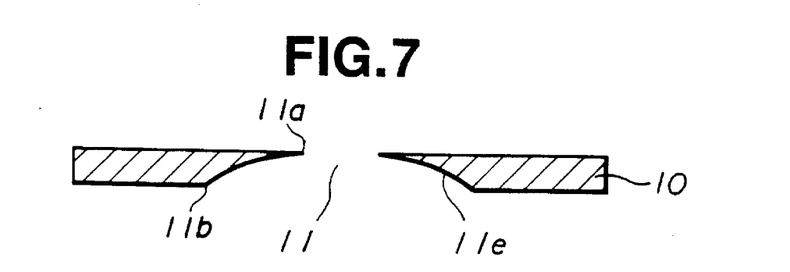
FIG. 7 is a cross-sectional view of another modification of a sheet mesh portion according to the invention.

In FIG. 7, showing a further modification of the embodiment, an area between the upper edge 11a and the lower edge 11b of the opening 11 of the sheet mesh 10 is formed as a concave circumferential portion 11e for further assuring that interference does not occur between the energy beam B and the material of the sheet mesh 10.

Figure 8:
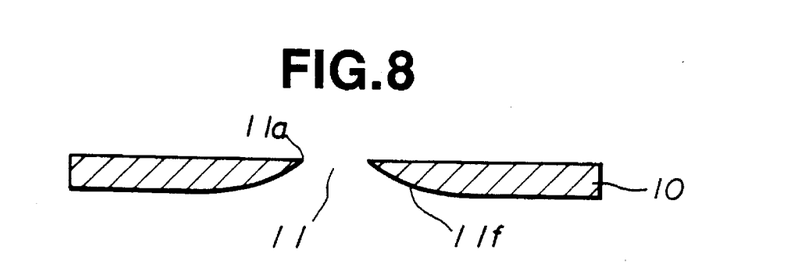
FIG. 8 is a cross-sectional view of a still further modification of a sheet mesh portion according to the invention.

Referring to FIG. 8, an entire lower area of the sheet mesh according to this modification is formed as an outwardly curved portion 11f.

Figure 9:
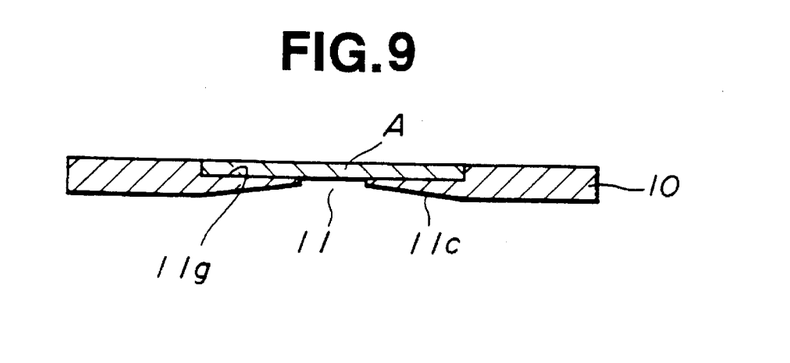
FIG. 9 is a cross-sectional view of an alternative modification of a sheet mesh portion, including a concave portion formed in a first surface thereof.

FIG. 9 shows an alternative formation of the sheet mesh 10 in which an upper surface 10a of the sheet mesh 10 is formed with a recessed portion 11g, which may be of a size corresponding to that of the wafer of sample material A so as to assuredly hold the sample material A in place during processing operations. The opening 11, the tapered portion 11c, etc., may be formed as in the above-described first embodiment, or according to any of the modifications thereof.

Hereinbelow, a second embodiment of a sheet mesh utilized for preparation of sample material A for processing according to the method of the invention will be explained in detail referring to FIGS. 10 and 11.

Figure 10:
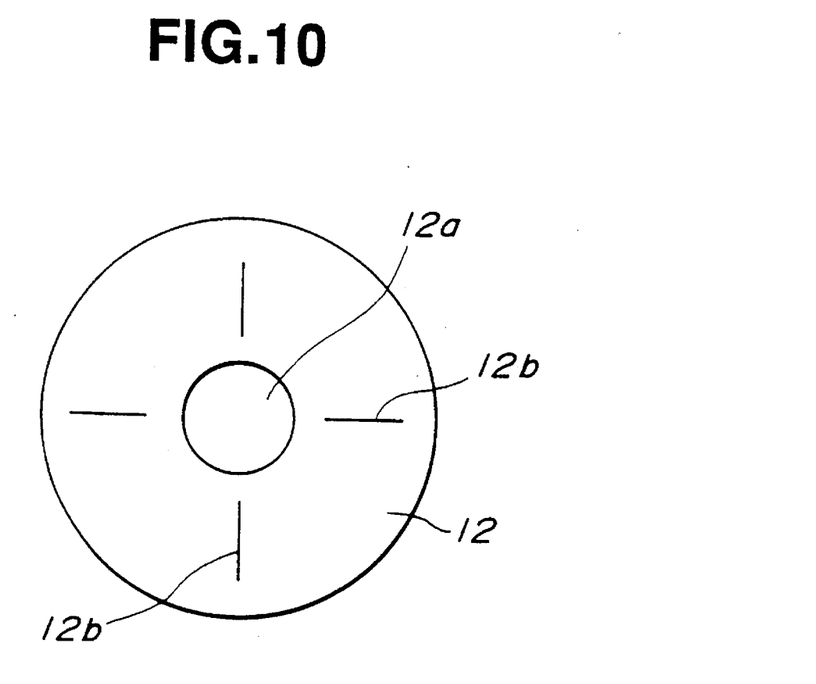
FIG. 10 is a plan view of a second embodiment of a sheet mesh according to the method of the invention.
Figure 11:
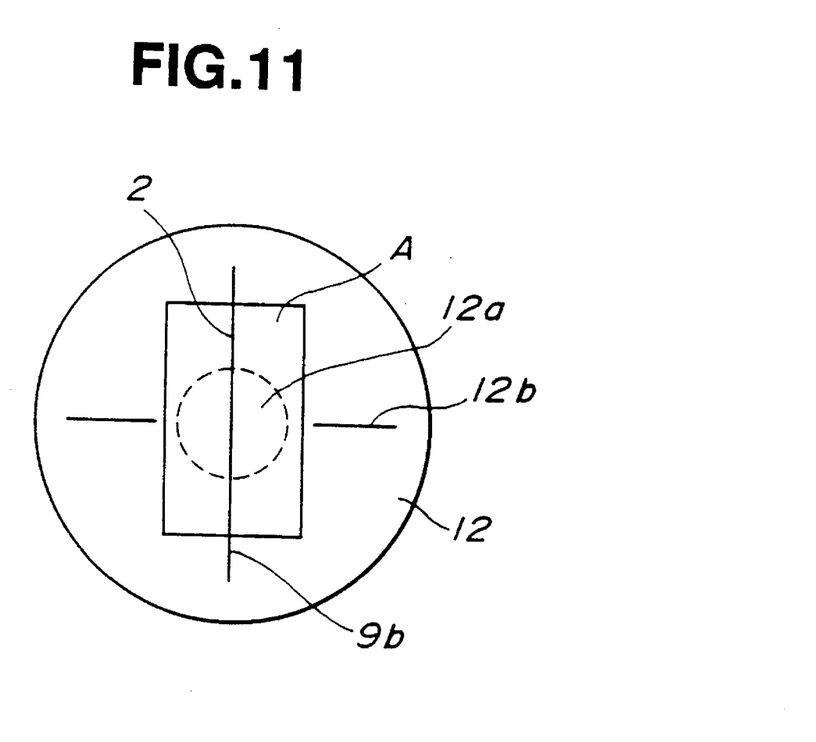
FIG. 11 is a plan view of the sheet mesh of FIG. 10, having a wafer of sample material positioned thereon.

FIG. 10 shows a plan view of an upper (first) surface of a sheet mesh 12. The elements of the sheet mesh 12 according to the present embodiment include a circular opening 12a provided in a center portion of the sheet mesh 12, and a plurality of line portions 12b which are radially aligned with a center of the opening 12a. As can be seen in FIG. 11, opposing line portions 12b, 12b are aligned 180° apart such that, when the sample material A is placed over the opening 12a, the line of the membrane layer 2, which runs through the axial center of the wafer of sample material A as described above, aligns with an opposing two of the line portions 12b. Thus, according to the above arrangement, accurate placement of the membrane layer 2 across the center of the opening is assured. Thus misalignment of the membrane layer during irradiation of the sample material, leading to formation of a defective sample such as shown in FIG. 17(B), is prevented.

It will be noted that this sheet mesh is also applicable for processing of sample material prepared according to the conventional method shown in FIGS. 14(A) and 14(B). Also, as in the conventional process shown in FIG. 14(D), the sheet mesh 12 with the sample material A thereon may be mounted on a rotation apparatus 8 and rotated under vacuum conditions while being irradiated by the energy beam B.

Figure 12:
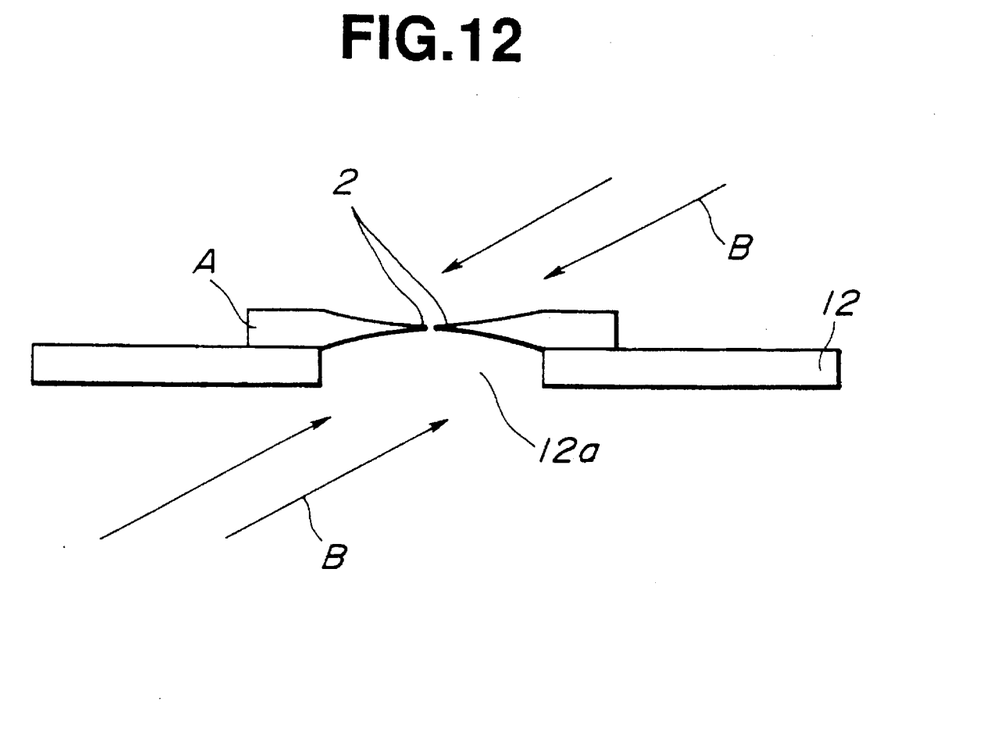
FIG. 12 is is cross-sectional view of a third embodiment of a sheet mesh according to the processing method for transmission electron microscope sample material of the invention.

According to the above described embodiment, and as shown in FIG. 12, optimal positioning of the membrane layer 2, the is, the portion of the sample material to be examined by the transmission electron microscope (not shown) is placed in the center of the irradiation opening 12a allowing the energy beam B to precisely irradiate the membrane layers for providing samples of the highest quality. According to this, a single membrane layer 2, or the center portion of the sample material prepared according to the method of the invention, comprising an adhesion layer binding two facing membrane layers 2, 2, between two substrate layers 1, 1 may be also optimally positioned for obtaining the most favorable irradiation characteristics.

Figure 13:
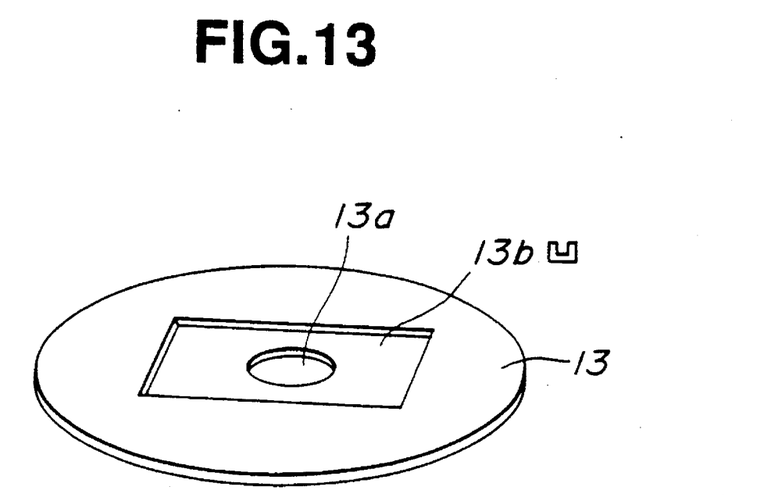

Referring now to FIG. 13, a perspective view of an alternative construction of a sheet mesh according to the second embodiment is shown. According to this, a sheet mesh 13 is provided with a central circular opening 13a, as with the previous embodiments. However, according to the present modification, on a first surface of the sheet mesh 13 on which the sample material A is to be placed, a recessed portion 13b is formed. That is, instead of the lines 12b of the previous embodiment, which provide visual means for positioning a membrane layer of the sample material, the present construction includes a recess determined at a size corresponding to that of the wafer of sample material A such that the sample material A is assuredly held in exactly the correct position. According to this, strict positioning of the membrane layer (or layers) is possible and displacement of the sample material A due to vibrations or the like cannot occur.

Thus, according to the present invention, uniform irradiation of sample material A, for examination under a transmission electron microscope is provided for creating high quality samples. The flow of the energy beam B irradiating the sample material A is not interfered with by portions of the sheet mesh and contamination of the sample material by the material of the sheet mesh is avoided.

Further, according to the method of the invention, preparation of high quality samples of membrane layer material which it was not possible to prepare according to conventional methods may be created with the present method since a protection layer is provided between the membrane layers and an adhesion layer for preventing degradation of the membrane layer material during processing.

Also, according to the invention, precise positioning of the portion of the sample material to be examined is reliably established. That is, the membrane layers, allowing high quality samples to be reliably produced without occurrence of defects.

While the present invention has been disclosed in terms of the preferred embodiment in order to facilitate better understanding thereof, it should be appreciated that the invention can be embodied in various ways without departing from the principle of the invention. Therefore, the invention should be understood to include all possible embodiments and modification to the shown embodiments which can be embodied without departing from the principle of the invention as set forth in the appended claims.

What is claimed is:

1. A sheet mesh for holding a sample material for use with a transmission electron microscope, comprising:

a metallic mesh having an opening provided in a substantially center portion thereof; and positioning determining means provided on a side of said sheet mesh on which said sample material is to be supported.

2. A sheet mesh as set forth in claim 1, further including a tapered portion formed at an edge of said opening in an area between said side of said sheet mesh on which said sample material is mounted and an opposite side of said sheet mesh.

3. A sheet mesh as set forth in claim 1, wherein said positioning determining means comprises a plurality of lines radially aligned with a center of said opening, opposing ones of said plurality of lines being aligned at 180°.

4. A sheet mesh as set forth in claim 1, wherein said positioning determining means comprises a recessed portion formed in one side of said sheet mesh at a predetermined position relative said opening, a size of said recessed portion corresponding to that of said sample material for snugly receiving same.

5. A method for processing sample material for use with a transmission electron microscope, comprising the steps of:

cutting a portion from said sample material to be used with said transmission electron microscope;

defining an opening in a layer of sheet mesh;

mounting said portion of said sample material on one side of said sheet mesh so as to be set at a predetermined position indicated by a positioning indication; and irradiating said sample material via an energy beam directed through said opening in said sheet mesh.

6. A method as set forth in claim 5, further including a step of rotating said sheet mesh during said irradiating step.

7. A method as set forth in claim 5, wherein said energy beam is an ion beam.

8. A method as set forth in claim 5, wherein said irradiating step is carried out by a plurality of energy beams.

9. A method for processing sample material for use with a transmission electron microscope, comprising the steps of:

providing first and second substrates;

applying a subject layer to at least one surface of said first substrate and a subject layer to at least one surface of said second substrate, applying a protective layer over said subject layer on said first substrate and a protective layer over said material layer on said second substrate;

joining said subject layer on said first substrate and said subject layer on said second substrate by joining each protective layer with an adhesion layer thereby forming a sample;

cutting said sample to a predetermined dimension such that said subject layer on said first substrate, said protective layer on said subject layer on said first substrate, said adhesion layer, said protective layer on said subject layer on said second substrate, and said subject layer on said second substrate together define a line formed substantially through a center of the cut sample;

forming an opening between first and second surfaces of a sheet mesh;

marking said first surface of said sheet mesh with a positioning indication;

mounting said sample over said opening according to said positioning indications; and irradiating said sample via an energy beam through said opening in said sheet mesh.

10. A method as set forth in claim 9, further including, after said forming step, a step of tapering a circumferential area of said opening between said first and second surfaces of said sheet mesh at an angle corresponding to an irradiation angle.

11. A method as set forth in claim 9, wherein said positioning indication comprises a plurality of radially extending line portions on said first surface of said sheet mesh.

* * * * *